(12) United States Patent
Tong et al.

(10) Patent No.: US 12,332,226 B2
(45) Date of Patent: Jun. 17, 2025

(54) REAL-TIME MEASURING DEVICE OF OXYGEN CONCENTRATION IN DROPLET ENVIRONMENT

(71) Applicant: SHANGHAI JIAO TONG UNIVERSITY, Shanghai (CN)

(72) Inventors: Lili Tong, Shanghai (CN); Zhichao Gao, Shanghai (CN); Xuewu Cao, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 314 days.

(21) Appl. No.: 18/182,253

(22) Filed: Mar. 10, 2023

(65) Prior Publication Data
US 2023/0204532 A1  Jun. 29, 2023

Related U.S. Application Data

(63) Continuation of application No. PCT/CN2022/105191, filed on Aug. 24, 2022.

(51) Int. Cl.
| | | |
|---|---|---|
| G01N 33/00 | (2006.01) | |
| G01N 27/04 | (2006.01) | |
| G01N 27/12 | (2006.01) | |
| G01N 27/406 | (2006.01) | |
| G01N 27/407 | (2006.01) | |
| G01N 27/409 | (2006.01) | |
| G01N 27/41 | (2006.01) | |
| G01N 27/419 | (2006.01) | |

(52) U.S. Cl.
CPC ....... *G01N 33/0011* (2013.01); *G01N 27/041* (2013.01); *G01N 27/12* (2013.01); *G01N 27/406* (2013.01); *G01N 27/4073* (2013.01); *G01N 27/409* (2013.01); *G01N 27/41* (2013.01); *G01N 27/419* (2013.01); *G01N 33/0016* (2013.01)

(58) Field of Classification Search
CPC .... G01N 27/12; G01N 27/406; G01N 27/407; G01N 27/4073; G01N 27/409; G01N 27/41; G01N 27/419; G01N 27/041; G01N 33/0011; G01N 33/0016
See application file for complete search history.

(56) References Cited

U.S. PATENT DOCUMENTS

| | | | | |
|---|---|---|---|---|
| 4,657,737 A | * | 4/1987 | Kampelmuhler | G01N 33/0013 436/160 |
| 5,694,835 A | * | 12/1997 | Mangina | H05B 6/6473 126/369 |
| 2013/0066564 A1 | * | 3/2013 | Forsyth | G01N 33/00 702/24 |

FOREIGN PATENT DOCUMENTS

CN  208399427 U  * 1/2019

* cited by examiner

*Primary Examiner* — Paul M. West
(74) *Attorney, Agent, or Firm* — CBM Patent Consulting, LLC

(57) ABSTRACT

A real-time measuring device of oxygen concentration in a droplet environment, comprising: a measurement pipeline, a gas-liquid separation structure installed inside a side of the gas inlet of the measurement pipeline, a pressure sensor, a zirconia oxygen concentration sensor with a built-in thermal resistor, a digital signal converter, a signal amplifier and a signal processing unit sequentially installed at the gas outlet of the measurement pipeline, wherein the pressure sensor, the thermal resistor and the zirconia oxygen concentration sensor are connected to the digital signal converter and the signal amplifier, respectively, and the signal processing unit obtains the amplified and AD converted zirconia oxygen concentration sensing signal, pressure sensing signal and the temperature sensing signal and calculates real-time oxygen concentration.

9 Claims, 5 Drawing Sheets

REAL-TIME MEASURING DEVICE OF OXYGEN CONCENTRATION IN DROPLET ENVIRONMENT

CROSS-REFERENCE TO RELATED APPLICATIONS

This application is the U.S. continuation application of International Application No. PCT/CN2022/105191 filed on 24 Aug. 2022 which designated the U.S. and claims priority to Chinese Application No. CN202111416407.9 filed on 26 Nov. 2021, the entire contents of each of which are hereby incorporated by reference.

TECHNICAL FIELD

The invention relates to a technology for direct measurement of oxygen concentration in a variable pressure environment where vapour, air and droplets are mixed, in particular to a real-time measuring device of oxygen concentration in a droplet environment.

BACKGROUND ART

During serious accident, a large amount of mixed gas of steam, hydrogen, etc. to be released into the containment. In order to evaluate the risk of hydrogen explosion in the containment, the dynamic oxygen content in the containment needs to be measured in real time. However, during the accident, some safety measures, such as external cooling, internal spraying, and fire spraying of the containment, will condense the steam in the containment, and some of the condensed droplets will float in the gas space, resulting in a large number of droplets with a diameter of about 0.2 mm floating in the containment. In addition, steam condensation will cause pressure changes. These lead to oxygen measurement difficult to realize.

Existing methods for oxygen measurement inside the containment include external sampling measurement and internal direct measurement. The external sampling measurement method samples and measures the gas inside the containment by extending a sampling tube into the containment. However, the sampling measurement process is complicated and data distortion is serious, so it cannot reflect the change of gas content inside the containment in time. Moreover, the external sampling measurement method will increase the risk of radioactive leakage of the containment because of the high content of radioactive substances in the containment.

The zirconia oxygen concentration sensor is a direct measurement device for oxygen concentration, which is designed and developed based on the principle that a potential difference will be formed on the surface of zirconia when oxygen partial pressures on two sides of zirconia are different in a high temperature environment (greater than 650° C.). The device is often used for oxygen concentration measurement in a normal pressure environment. Because the zirconia oxygen concentration sensor needs to be heated to 650° C. when used. When the measured gas contains droplets, the high-temperature zirconia sensor will heat the droplets in the carrier gas and vaporize them into vapour, which will change the gas composition in the carrier gas and affect the measurement accuracy of the sensor. Therefore, the existing zirconia oxygen concentration sensor cannot be directly used for internal measurement of oxygen concentration in a droplet environment.

SUMMARY

Aiming at the above shortcomings of the prior art, the invention proposes a real-time measuring device of oxygen concentration in a droplet environment, which can measure the oxygen concentration in real time in a variable pressure environment where vapour, air and droplets are mixed.

The invention is realized by the following technical scheme.

The invention relates to a real-time measuring device of oxygen concentration in a droplet environment, comprising: a measurement pipeline, a gas-liquid separation structure installed inside a side of the gas inlet of the measurement pipeline, a pressure sensor, a zirconia oxygen concentration sensor with a built-in thermal resistor, a digital signal converter, a signal amplifier and a signal processing unit sequentially installed at the gas outlet of the measurement pipeline, wherein the pressure sensor, the thermal resistor and the zirconia oxygen concentration sensor are connected to the digital signal converter and the signal amplifier respectively, and the signal processing unit obtains the amplified and AD converted zirconia oxygen concentration sensing signal, pressure sensing signal and the temperature sensing signal and calculates real-time oxygen concentration.

The gas-liquid separation structure is any of the following forms:
  A. comprises a support column located in the center, fin-shaped droplet guide plates arranged around the support column, and multiple burrs arranged on the guide plates, wherein when the measured gas containing droplets enters the gas-liquid separation structure through the gas inlet, the droplets stay on the burrs of the gas-liquid separation structure through inertial collision with the burrs in the flowing process, and are guided to the droplet guide plates and flow out of the flow field through the droplet guide plates, so that the droplets in the measured gas are removed; or
  B. comprises a support column located in the center, a spiral hole located in the support column and needle-shaped structures fixed on the spiral hole, wherein the support column is a stainless steel hollow cylinder, the upper part of the cylinder is sealed and the lower part is open, a wall surface of the stainless steel hollow cylinder is provided with the spiral hole, and multiple needle-like structures are fixed on the spiral hole, and the needle-like structures are conical needles.

The diversion structure is a fin-shaped droplet guide plate or a spiral diversion hole.

The support column is a stainless steel hollow cylinder, an upper part of the cylinder is sealed and the lower part is open.

The number of turns of the droplet guide plates or spiral diversion holes around the support column is 4-8.

The burrs are fixed on the droplet diversion structure, and the number of burrs in each circle is not less than 500.

The burrs are tilted upward and have an included angle of 3-5° with the diversion structure, so that the separated droplets are guided to the diversion structure and flow out of the measurement pipeline after entering the support column.

A water retaining ring is arranged on an inner wall surface of the measurement pipeline behind the gas-liquid separation structure.

The zirconia oxygen concentration sensor comprises a zirconia inner tube, a zirconia heater arranged outside and inside the zirconia inner tube, a zirconia intra-tube thermal resistor which is arranged inside the zirconia inner tube, a reference gas is arranged in the zirconia inner tube, and the zirconia intra-tube thermal resistor is used for measuring the temperature of the reference gas.

The outside of the zirconia heater of the zirconia oxygen concentration sensor is provided with a droplet shielding piece for collecting droplets dropping into the measurement pipeline from an gas outlet, and the collected droplets are directly heated into steam, which flows out of the measurement pipeline with a measured fluid through the gas outlet.

The signal processing unit comprises a single chip microcomputer and a power supply, the single chip microcomputer corrects the oxygen concentration signal in real time according to the pressure sensing signal and the thermal resistance signal, and the corrected oxygen concentration signal, the pressure signal and the temperature signal are displayed and stored by a signal storage display.

The real-time correction comprises:
(1) introducing air with an oxygen concentration of $x_1$ and a mass of M into a zirconia tube, with a known volume of V, of the zirconia oxygen concentration sensor as a reference gas;
(2) measuring a real-time absolute pressure $P_2$ in a gas environment to be measured by the pressure sensor, and converting a voltage signal generated by the pressure sensor into a digital signal by the digital signal converter to obtain the absolute pressure $P_2$;
(3) measuring the temperature of the reference gas in the tube by a zirconia intra-tube thermal resistor, converting a resistance signal generated by the thermal resistor into a digital signal by the digital signal converter to obtain the temperature of the reference gas T, and obtaining the pressure of the reference gas $$P_1 = \frac{MRT}{V}$$

according to an ideal gas equation;
(4) measuring the oxygen concentration of the measured gas by the zirconia oxygen concentration sensor, amplifying a micro voltage signal generated by the zirconia oxygen concentration sensor by the signal amplifier and then transmitting the same to the digital signal converter to be converted into a digital signal, so as to obtain the uncorrected oxygen concentration; and
(5) using the following formula to correct the digital signal measured by the zirconia oxygen concentration sensor, where the corrected actual oxygen concentration is:

$$x_2 = \frac{P_1}{P_2} x_1 = \frac{MRT}{VP_2} x_1.$$

Technical Effects

The invention can separate and remove droplets in the measured gas based on mechanical principles before the measured gas approaches the zirconia oxygen concentration sensor, so that the zirconia oxygen concentration sensor can measure the oxygen concentration in the droplet environment in real time. With a simple structure, the oxygen concentration signal in the variable pressure environment is corrected using the pressure signal, and the oxygen concentration of measured gas in the range of 0-21% can be measured in real time in a varying pressure droplet environment.

In the figures: 1, measurement pipeline; 2, gas-liquid separation structure; 201, support column; 202, droplet guide plate; 203, Burrs; 204, fixing and supporting plate; 205, spiral hole; 3, gas outlet; 4, droplet shielding piece; 5, pressure sensor; 6, gas inlet; 7. water retaining ring; 8, zirconia oxygen concentration sensor; 801, zirconia inner tube; 802, zirconia intra-tube thermal resistor; 803, zirconia heater; 9, signal amplifier; 10, digital signal converter; 11, signal processing unit; 12, signal storage display.

DETAILED DESCRIPTION OF THE INVENTION

Embodiment 1

Figure 1:
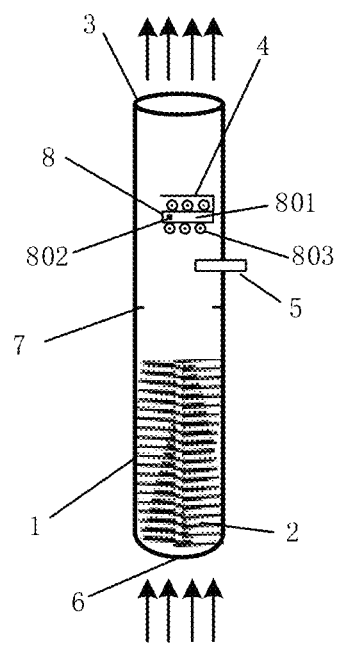
FIG. 1 is a structural diagram of the invention.
Figure 8:
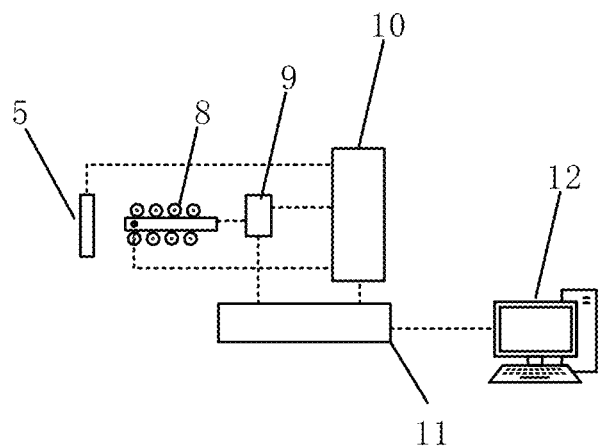
FIG. 8 is a diagram of a signal processing mode of the invention.

As shown in FIGS. 1 and 8, this embodiment relates to a real-time measuring device of oxygen concentration in a droplet environment, which comprises a measurement pipeline 1, a gas-liquid separation structure 2 arranged inside a side, provided with an gas inlet, of the measurement pipeline, and a pressure sensor 5 and a zirconia oxygen concentration sensor 8 sequentially arranged at a side provided with an gas outlet. The zirconia oxygen concentration sensor needs to be heated to 650° C. in use, which is much higher than the ambient temperature, therefore, affected by the buoyancy force generated by the expansion of heated gas, the gas in the measurement pipeline is continuously discharged from an gas outlet, and the measured gas in the environment is guided to flow into the measurement pipeline, in this way, the measured gas is passively driven into the measurement pipeline. The zirconia oxygen concentration sensor 8 is provided with a zirconia intra-tube thermal resistor 802 inside. The pressure sensor 5, the zirconia intra-tube thermal resistor 802 and the zirconia oxygen concentration sensor 8 are connected to a digital signal converter 10 and a signal amplifier 9. A signal processing unit 11 calculates the real-time oxygen concentration according to a zirconia oxygen concentration sensing signal which has be amplified and then converted into a digital signal, a pressure sensing signal and a temperature sensing signal.

Figure 2:
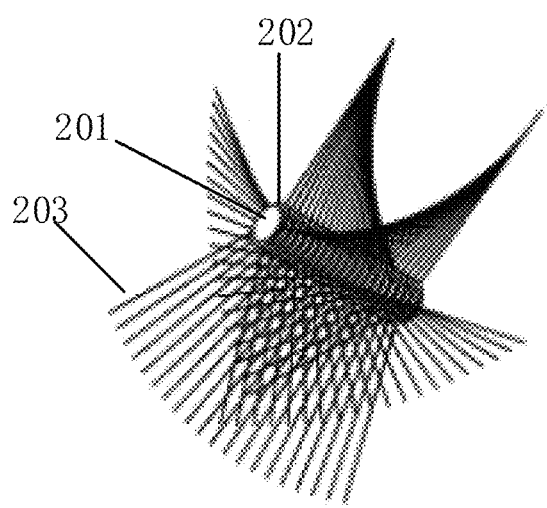
FIG. 2 is a diagram of a gas-liquid separation structure of the invention.
Figure 3:
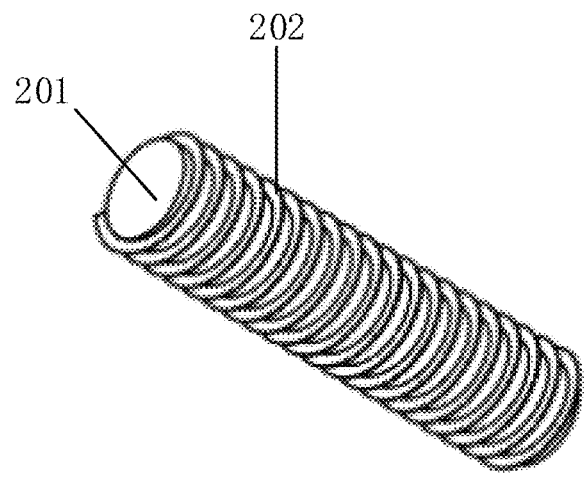
FIG. 3 is a structural diagram of a droplet guide plate of a gas-liquid separation structure in Embodiment 1 of the invention.

As shown in FIGS. 2 and 3, the gas-liquid separation structure 2 comprises a support column 201 located in the center, fin-shaped droplet guide plates 202 arranged around the support column, and burrs 203 fixed on the guide plates, and when the measured gas containing droplets enters the gas-liquid separation structure 2 through the gas inlet, the droplets stay on the burrs 203 of the gas-liquid separation structure through inertial collision with the burrs 203 in the flowing process, and are guided to the droplet guide plates 202 and flow out of the flow field through the droplet guide plates 202, so that the droplets in the measured gas can be removed.

The measurement pipeline 1 is a stainless steel pipe with an inner diameter of 20 mm and a length of 200 mm.

Figure 5:
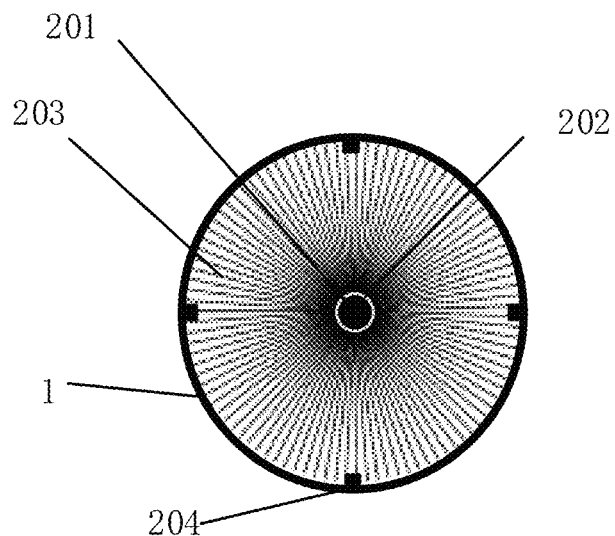
FIG. 5 is a zirconia oxygen concentration sensor with a droplet shielding piece according to the invention.

As shown in FIG. 5, the diameter of the gas-liquid separation structure 2 is the same as the inner diameter of the measurement pipeline 1, fixing and supporting plates 204 are welded to an entrance of the measurement pipeline 1 for fixing and supporting the gas-liquid separation structure 2, and the number of the fixing and supporting plates 204 is more than two.

The zirconia oxygen concentration sensor 8 comprises a zirconia inner tube 801, and a zirconia heater 803 which is arranged outside and inside the zirconia inner tube and a zirconia intra-tube thermal resistor 802 which is arranged inside the zirconia inner tube, wherein normal pressure air with a mass of M and an oxygen concentration of $x_1$ is arranged in the zirconia inner tube 801 as a reference gas, the zirconia intra-tube thermal resistor 802 is used for measuring the temperature of the reference gas, and the heating temperature of the zirconia oxygen concentration sensor 8 is 650° C.

Figure 6:
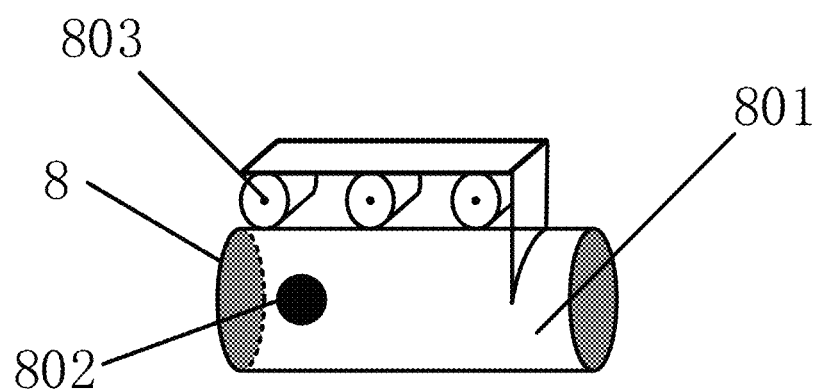
FIG. 6 is a cross-sectional view of a water retaining ring.

As shown in FIG. 6, the upper part of the zirconia heater 803 of the zirconia oxygen concentration sensor 8 is provided with a droplet shielding piece 4 for collecting droplets dropping into the measurement pipeline from an gas outlet, and the collected droplets are directly heated into steam, which flows out of the measurement pipeline with a measured fluid through the gas outlet.

The distance between the zirconia oxygen concentration sensor 8 and the top of the gas-liquid separation structure 2 is 80 mm.

As shown in FIG. 3, the support column 201 of the gas-liquid separation structure 2 is a stainless steel hollow cylinder, the upper part of the cylinder is sealed and the lower part is open, and the stainless steel hollow cylinder has a diameter of 6 mm and a length of 60 mm.

The fin-shaped droplet guide plates 202 are wound around the stainless steel hollow cylinder, and the number of turns of the droplet guide plates is 4-8.

Figure 4:
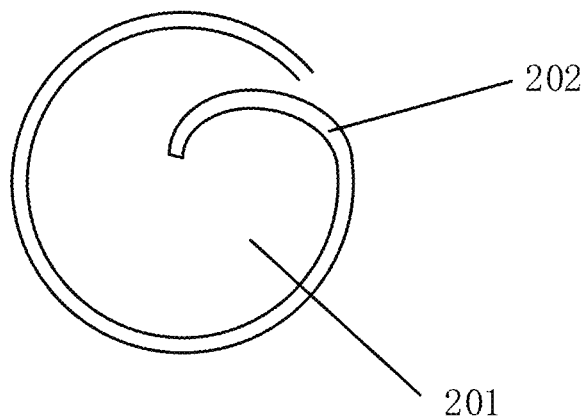
FIG. 4 is a bottom view of a structure of the invention.

As shown in FIG. 4, the fin-shaped guide plate 202 extends into the support column at a lower end of the hollow support column 201 through a small hole in a wall surface of the support column, and leads droplets to the center of the support column 201, and then the droplets flow out of the measurement pipeline 1.

As shown in FIG. 2, multiple burrs 203 are fixed on the droplet guide plates 202. The burrs have a conical needle-like structure. The burrs 203 are slightly tilted upward and have an included angle of 3-5° with the droplet guide plates 202, so that the separated droplets are guided to the droplet guide plates 202 and flow out of the measurement pipeline under gravity.

The burrs are arranged on the droplet guide plate 202 at equal intervals, and the number of burrs on each circle of droplet guide plates is not less than 500.

Figure 7:
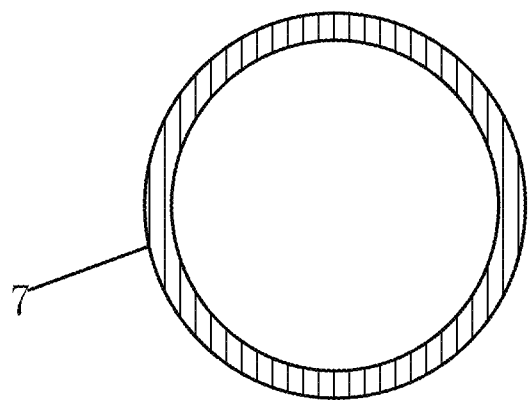
FIG. 7 is a partial structural diagram of a droplet guide plate at the bottom of a support column in Embodiment 1.

Considering that the droplets on the inner wall surface of the measurement pipeline 1 may be driven by the measured airflow and slide upward with the airflow, a water retaining ring 7 is arranged on the inner wall surface of the pipeline behind the gas-liquid separation structure 2, as shown in FIGS. 1 and 7, and the thickness of the water retaining ring is 2 mm.

The distance between the zirconia oxygen concentration sensor 8 and the gas-liquid separation structure 2 is 80 mm.

The signal processing unit 11 comprises a single chip microcomputer and a power supply, the single chip microcomputer corrects the oxygen concentration signal in real time according to the pressure sensing signal and the thermal resistance signal, and the corrected oxygen concentration signal, the pressure signal and the temperature signal are displayed and stored by a signal storage display 12.

The real-time correction comprises:
1) introducing air with an oxygen concentration of $x_1$ and a mass of M into a zirconia inner tube 801, with a volume of V, of the zirconia oxygen concentration sensor 8 as a reference gas;
2) measuring a real-time absolute pressure $P_2$ in a gas environment to be measured by the pressure sensor 5, and converting a voltage signal generated by the pressure sensor 5 into a digital signal by the digital signal converter 10 to obtain the absolute pressure $P_2$;
3) measuring the temperature of the reference gas in the tube by a zirconia intra-tube thermal resistor 802, converting a resistance signal generated by the thermal resistor into a digital signal by the digital signal converter 10 to obtain the temperature of the reference gas T, and obtaining the pressure of the reference gas $$P_1 = \frac{MRT}{V}$$

according to an ideal gas equation;
4) measuring the oxygen concentration of the measured gas by the zirconia oxygen concentration sensor 8, amplifying a micro voltage signal generated by the zirconia oxygen concentration sensor 8 by the signal amplifier 9 and then transmitting the same to the digital signal converter 10 to be converted into a digital signal, so as to obtain the uncorrected oxygen concentration; and
5) using the following formula to correct the digital signal measured by the zirconia oxygen concentration sensor 8 in the signal processing unit 11, where the corrected actual oxygen concentration is:

$$x_2 = \frac{P_1}{P_2}x_1 = \frac{MRT}{VP_2}x_1.$$

Embodiment 2

Figure 9:
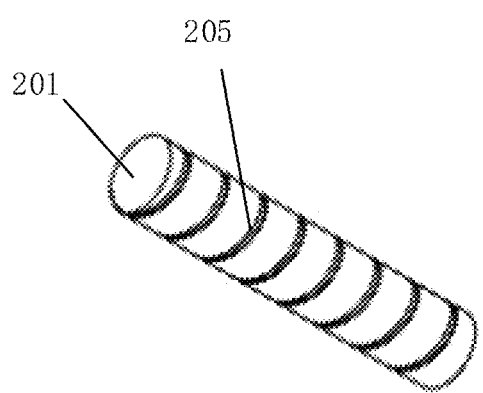
FIG. 9 is a diagram of a gas-liquid separation structure with spiral hole type burrs described in Embodiment 2.

As shown in FIG. 9, the gas-liquid separation structure 2 in this embodiment comprises: a support column 201 located in the center, a spiral hole 205 located in the support column 201 and needle-shaped structures 203 fixed on the spiral hole, wherein the support column 201 is a stainless steel hollow cylinder, the upper part of the cylinder is sealed and the lower part is open, and the stainless steel hollow cylinder has a diameter of 6 mm and a length of 60 mm.

The wall surface of the stainless steel hollow cylinder is provided with a spiral hole 205. The number of turns of the spiral hole is 4-8, and the diameter of the hole is 1 mm.

Multiple needle-like structures 203 are fixed on the spiral hole 205. The needle-like structures 203 are conical needles, the tips of which are slightly tilted upwards and have an included angle of 3-5° with the spiral hole 205.

The needle-like structure 203 extends into the support column 201 by 1 mm through the spiral hole 205, so as to guide the separated droplets into the support column 201. Because the support column 201 has a sealed upper part and an open bottom, the airflow in the support column is stationary, and the droplets flowing into the support column 201 will not be entrained by the airflow, and can flow out of the measurement pipeline 1 under gravity.

The needle-like structures 203 are arranged on the spiral hole 205 at equal intervals, and the number of needle-like structures on each circle of spiral hole is not less than 500.

The diameter of the supporting gas-liquid separation structure 2 is the same as the inner diameter of the measurement pipeline 1, fixing and supporting plates 204 are welded to the entrance of the measurement pipeline 1 for fixing and supporting the gas-liquid separation structure 2, and the number of the fixing and supporting plates 204 is more than 2.

Practical experiments show that in an environment with a pressure changing range of 0-0.5 MPa where droplets, vapour and air are mixed, the oxygen concentration in the ambient gas can be directly and accurately measured by using the above method, and the measurable range of oxygen concentration is 0-21%.

Compared with the prior art, this device allows the measured gas to automatically flow into the measurement pipeline through a special structural design, and can remove the droplets in the measured gas through the gas-liquid separation structure. This device solves the problem of inaccurate measurement of a conventional zirconia oxygen concentration gauge in an environment containing droplets, and realizes online variable pressure measurement of the zirconia oxygen concentration gauge in a variable pressure environment by means of a correction method.

The above specific implementation can be partially adjusted by those skilled in the art in different ways without departing from the principle and purpose of the invention. The scope of protection of the invention is subject to the claims and is not limited by the above specific implementation, and each implementation scheme within its scope is bound by the invention.

What is claimed is:

1. A real-time measuring device of oxygen concentration in a droplet environment, comprising:
    a measurement pipeline,
    a gas-liquid separation structure installed inside a side of a gas inlet of the measurement pipeline,
    a pressure sensor, a zirconia oxygen concentration sensor with a built-in thermal resistor, a digital signal converter, a signal amplifier and a signal processing unit sequentially installed at the gas outlet of the measurement pipeline, wherein
    the pressure sensor, the thermal resistor and the zirconia oxygen concentration sensor are connected to the digital signal converter and the signal amplifier, respectively, and the signal processing unit obtains the amplified and AD converted zirconia oxygen concentration sensing signal, pressure sensing signal and a temperature sensing signal and calculates real-time oxygen concentration;
    wherein the zirconia oxygen concentration sensor comprises a zirconia inner tube, a zirconia heater arranged outside and inside the zirconia inner tube and a zirconia intra-tube thermal resistor, a reference gas is arranged in the zirconia inner tube, and the zirconia intra-tube thermal resistor is used for measuring the temperature of the reference gas.

2. The real-time measuring device according to claim 1, wherein the gas-liquid separation structure is either:
    i. comprises a support column located in the center, fin-shaped droplet guide plates arranged around the support column, and multiple burrs arranged on the guide plates, wherein when the measured gas containing droplets enters the gas-liquid separation structure through the gas inlet, the droplets stay on the burrs of the gas-liquid separation structure through inertial collision with the burrs in the flowing process, and are guided to the droplet guide plates and flow out of the flow field through the droplet guide plates, in order to remove the droplets in the measured gas; or
    ii. comprises a support column located in the center, a spiral hole located in the support column and needle-shaped structures fixed on the spiral hole, wherein the support column is a stainless steel hollow cylinder, and the upper part of the cylinder is sealed while the lower part is open, and the wall surface of the stainless steel hollow cylinder is provided with the spiral hole, and multiple needle-like structures are fixed on the spiral hole, and the needle-like structures are conical needles.

3. The real-time measuring device according to claim 2, wherein the support column is of a solid cylindrical structure, and the droplet guide plates around the support column for 4-8 turns.

4. The real-time measuring device according to claim 3, wherein the burrs are fixed on the droplet guide plates, and the burrs are tilted upward and have an included angle of 3-5° with the droplet guide plates, so that the separated droplets can be guided to the droplet guide plates and flow out of the measurement pipeline under gravity.

5. The real-time measuring device according to claim 3, wherein a water retaining ring is installed on the inner wall surface of the measurement pipeline behind the gas-liquid separation structure.

6. The real-time measuring device according to claim 1, wherein outside of the zirconia heater of the zirconia oxygen concentration sensor is provided with a droplet shielding piece for collecting droplets dropping into the measurement pipeline from an gas outlet, and the collected droplets are directly heated into steam, which flows out of the measurement pipeline with the measured gas through the gas outlet.

7. The real-time measuring device according to claim 1, wherein the outside of the zirconia heater of the zirconia oxygen concentration sensor is provided with a droplet shielding piece for collecting droplets dropping into the measurement pipeline from an gas outlet, and the collected droplets are directly heated into steam, which flows out of the measurement pipeline with the measured gas through the gas outlet.

8. The real-time measuring device according to claim 1, wherein the signal processing unit comprises a single chip microcomputer and a power supply, the single chip microcomputer correcting the oxygen concentration signal in real time according to the pressure sensing signal and the temperature signal, and the corrected oxygen concentration signal, the pressure signal and the temperature signal are displayed and stored by a signal storage display.

9. The real-time measuring device according to claim 8, wherein the correcting the oxygen concentration signal in real time comprises:
    (i) introducing air with an oxygen concentration of $x_1$ and a mass of M into the zirconia tube, with a known volume of V, of the zirconia oxygen concentration sensor as a reference gas;

(ii) measuring a real-time absolute pressure $P_2$ in a gas environment to be measured by the pressure sensor, and converting a voltage signal generated by the pressure sensor into a digital signal by the digital signal converter to obtain the absolute pressure $P_2$;

(iii) measuring the temperature of the reference gas in the tube by a zirconia intra-tube thermal resistor, converting a resistance signal generated by the thermal resistor into a digital signal by the digital signal converter to obtain the temperature of the reference gas T, and obtaining the pressure of the reference gas according to the ideal gas equation:

$$P_1 = \frac{MRT}{V};$$

(iv) measuring the oxygen concentration of the measured gas by the zirconia oxygen concentration sensor, amplifying a micro voltage signal generated by the zirconia oxygen concentration sensor by the signal amplifier and then transmitting the same to the digital signal converter to be converted into a digital signal, so as to obtain the uncorrected oxygen concentration; and (v) using the following formula to correct the digital signal measured by the zirconia oxygen concentration sensor, where the corrected actual oxygen concentration is:

$$x_2 = \frac{P_1}{P_2}x_1 = \frac{MRT}{VP_2}x_1.$$

\* \* \* \* \*